United States Patent [19]

Moss

[11] 3,997,971
[45] Dec. 21, 1976

[54] UNIVERSAL ORTHODONTIC HEAD GEAR

[76] Inventor: Dan Moss, 247 Ridge Road, Cedar City, Utah 84720

[22] Filed: July 28, 1975

[21] Appl. No.: 599,714

[52] U.S. Cl. .............................................. 32/14 B
[51] Int. Cl.$^2$ .......................................... A61C 7/00
[58] Field of Search .................................. 32/14 D

[56] References Cited
UNITED STATES PATENTS 523,192  7/1894  Angle .............................. 32/14 D Primary Examiner—Robert Peshock

[57] ABSTRACT

An orthodontic head gear is disclosed for use in applying traction forces to produce posterior movement of the maxillary molars and arch. The head gear includes an arch bow which is adapted to conform to the contour of the dental arch of the patient undergoing orthodontic treatment and an associated face bow to which are applied the traction forces. A coupling is attached between the arch bow and face bow which is rotatable in orthogonal directions. The rotatable coupling comprises a ball and socket joint which is selectively positionable within and without of a plane bisecting the arch bow into symetric parts.

5 Claims, 2 Drawing Figures

UNIVERSAL ORTHODONTIC HEAD GEAR

BACKGROUND OF THE INVENTION

1. Field of the Invention

The invention relates to an orthodontic head gear used for applying traction forces for producing posterior movement of the maxillary molars and arch. More particularly, the invention relates to orthodontic head gear which may be used to selectively produce bilateral or unilateral posterior movement of the maxillary molars and arch independent of the movement of the patient's head without applying a substantial force to the maxillary molars and arch in a direction not parallel to the direction of posterior movement.

2. Description of the Prior Art

Angle, U.S. Pat. No 523,192, discloses an orthodontic head gear having an arch bow which is attached by a ball and socket joint to a face bow. The ball and socket joint is permanently mounted in a plane which bisects the arch bow into symetric parts. Unlike the present invention, Angle's head gear may not be used for producing unilateral posterior movement of the maxillary molars and arch.

Knapp, U.S. Pat. No. 664,412, discloses an orthodontic head gear incorporating a pair of rotatable joints that are permanently connected respectively to an arch bow and a face bow of the head gear in a plane bisecting the arch bow into symetric parts. The individual rotatable joints are rotatable in a single plane but are disposed with respect to the arch and face bow to permit universal movement of the arch bow with respect to the face bow. Knapp's head gear, unlike the present invention, may not be used for producing unilateral posterior movement of the maxillary molars and arch.

MacDowell, U.S. Pat. No. 741,687, discloses an orthodontic head gear having an arch bow which is attached to a face bow by a pivotal coupling disposed in a plane bisecting the arch bow into symetric parts. Unlike the present invention, MacDowell's head gear may not be used for producing unilateral posterior movement of the maxillary molars and arch.

Broussard et al., U.S. Pat. No. 3,866,322, disclose an orthodontic head gear having a rotatable coupling disposed between an arch bow and a face bow. The coupling is not rotatable in orthogonal directions. The rotatable coupling is symetrically disposed with respect to a plane bisecting the arch bow into symetric parts. Broussard et al's apparatus may not be used for producing unilateral posterior movement of the maxillary molars and arch.

A commercially available orthodontic head gear sold by Unitek Corporation as the "Unilateral Zwemer Swivel" permits the unilateral posterior movement of the maxillary molars and arch. This device incorporates a swivel coupling between a point of attachment of a face bow to an arch bow. The coupling is not rotatable in orthogonal directions. Unlike the present invention, this device may not be selectively used for producing unilateral or bilateral posterior movement of the maxillary molars and arch. Moreover, the swivel coupling does not permit movement of the patient's head in orthogonal directions without the application of a substantial force to the maxillary molars and arch in a direction not parallel to the direction of posterior movement of the maxillary molars and arch.

SUMMARY OF THE INVENTION

The disadvantages and limitations of the prior art are obviated by the present invention which may be used for producing the selective unilateral or bilateral posterior movement of the maxillary molars and arch while permitting patients to rotate their heads in orthogonal directions without the application of substantial forces to the maxillary molars and arch in directions not parallel to the direction of the posterior movement.

DETAILED DESCRIPTION OF THE INVENTION

Figure 1:
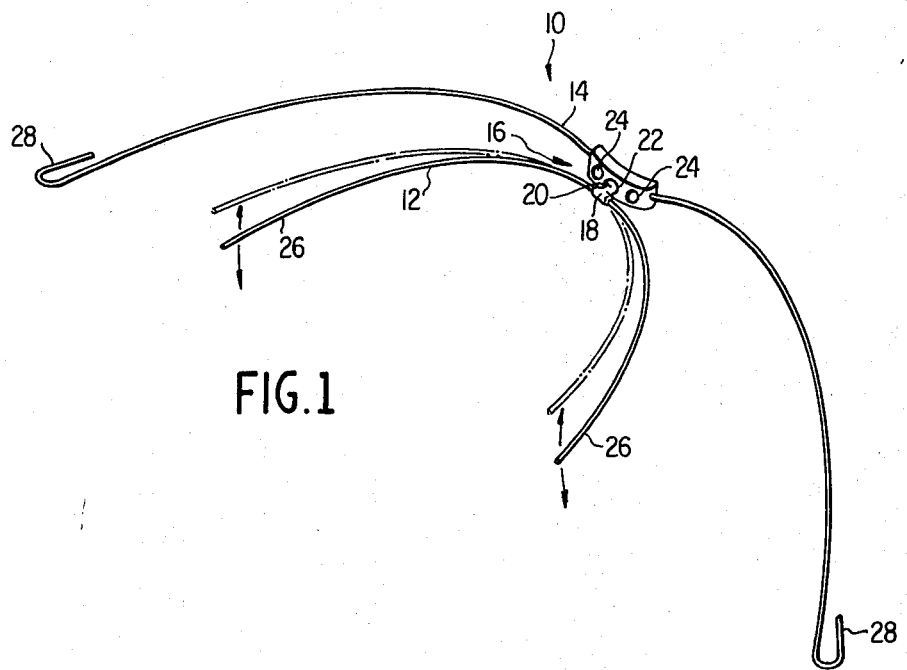
FIG. 1 is a perspective view of the present invention.
Figure 2:
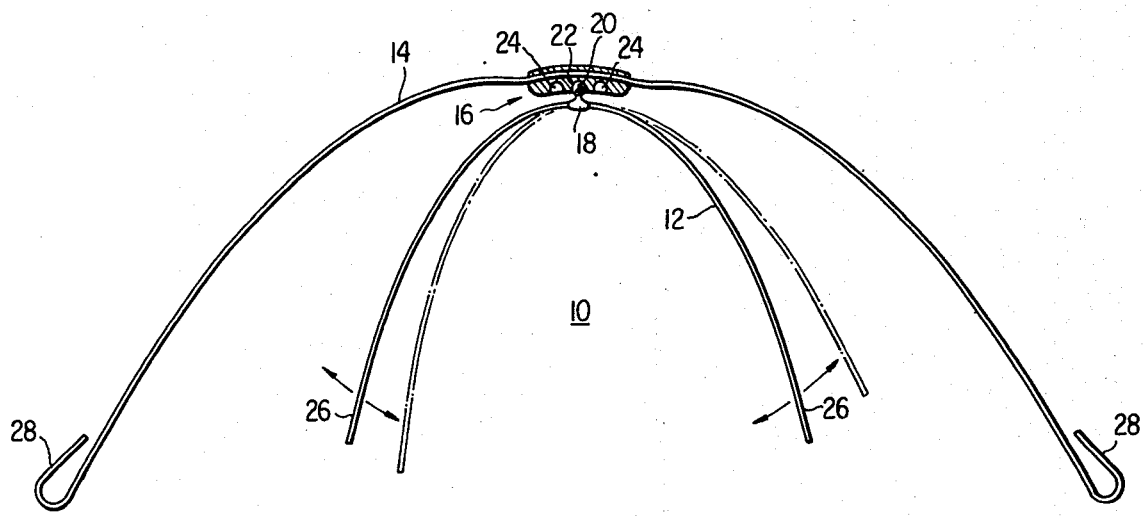
FIG. 2 is a plane view of the present invention.

Referring to FIGS. 1 and 2, the invention includes an orthodontic head gear 10 having a generally curved arch bow 12 which is adapted to conform to the contour of a dental arch of a patient undergoing orthodontic treatment, a generally curved face bow 14 which is adapted to be disposed outside of the patient's mouth and an orthogonally rotatable coupling member 16 which is connected to arch bow 12 and face bow 14. The coupling member 16 comprises a member 18 having a ball 20 disposed on its end and associated sockets 22 and 24 which are mounted on the inside of the face bow 14 respectively within and without of a plane which bisects the arch bow 12 into symetric parts. The outside sockets 24 are attached symetrically to the face bow 14 with respect to the socket 22. The member 18 is also mounted within a plane which bisects the arch bow 12 into symetric parts. The diameter of the sockets 22 and 24 is slightly smaller than the diameter of the ball 20 so that the ball must be forced into and thereafter will be retained within one of the sockets 22 or 24. The ends 26 of the arch bow 12 are adapted to be inserted into buccal tubes not shown which are attached to orthodontic bands that are anchored to the molars. The hooked ends 28 are adapted to be coupled to an elastic type band not shown which fits around the neck of the patient to apply posterior traction force to the maxillary molars and arch.

The ball 20 and associated sockets 22 and 24 form a ball and socket joint which permits motion of the face bow 14 in orthogonal directions with respect to the arch bow 12. The ball and socket joint permits patients wearing the orthodontic head gear 10 to turn their heads without applying a substantial amount of traction force to the arch bow 12 in directions not parallel to the direction of posterior movement of the maxillary molars and arch.

The selective bilateral or unilateral movement of the maxillary molars and arch are produced in the following manner. When the head gear 10 is worn so that the ball 20 is inserted into the centrally disposed socket 22, the posterior traction force is uniformly distributed to both sides of the dental arch. When the head gear 10 is worn so that ball 20 is inserted into one of the noncentrally disposed sockets 24, the posterior traction force is applied to a greater extent to the side of the face bow 14 on which ball 20 is inserted to produce a unilateral traction force on that side.

In its preferred construction the orthodontic head gear of the present invention has the following characteristics. The arch bow 12 consists of a stainless steel wire having a diameter ranging from 10.16 to 12.95 millimeters. The face bow 14 consists of a stainless steel wire having a diameter ranging from 12.70 to 19.50 millimeters. The ball 20 ranges from 2 to 10 millimeters in diameter. The member 18 is soldered to the arch bow 12.

While the invention has been described in terms of a preferred embodiment, numerous modifications may be made thereto without departing from the spirit and scope of the invention. It is intended that these modifications fall within the scope of the appended claims.

What I claim is:

1. An orthodontic head gear comprising:
   a. an arch bow which is adapted to conform to the contour of a dental arch of a patient undergoing orthodontic treatment;
   b. a face bow which is adapted to be positioned outside of the patient's mouth from a position in front of the mouth to a position to the rear thereof; and
   c. a rotatable coupling coupled to said arch bow and to said face bow, said coupling being rotatable in two orthogonal directions and being selectively positionable at a point which lies within a plane bisecting the arch bow into symetric parts and at a plurality of points outside of the plane.

2. An orthodontic head gear as recited in claim 1 wherein said rotatable coupling comprises:
   a. a ball and socket joint.

3. An orthodontic head gear as recited in claim 2 wherein:
   a. said ball of said ball and socket joint is attached to said arch bow at a point lying within the plane which bisects said arch bow into symetric parts; and
   b. wherein a plurality of sockets are attached to said face bow on the inside thereof, one of said sockets being attached at a point within said plane bisecting said arch bow into symetric parts and the remainder of said sockets being attached to said face bow outside of said plane bisecting said arch bow into symetric parts.

4. An orthodontic head gear as recited in claim 3 wherein:
   a. said remainder of sockets are symetrically attached to said face bow with respect to said one socket which is attached to said face bow within said plane which bisects said bow into symetric parts.

5. An orthodontic head gear as recited in claim 4 further comprising:
   a. a member having two ends, one of said ends being attached to said arch bow in a plane which bisects said arch bow into symetric parts and the other of said ends being attached to said ball of said ball and socket joint.

* * * * *